United States Patent [19]
Don Michael

[11] Patent Number: 5,380,284
[45] Date of Patent: Jan. 10, 1995

[54] OBSTRUCTION DISSOLUTION CATHETER WITH VARIABLY EXPANDING BLOCKING BALLOONS AND METHOD OF USE

[76] Inventor: T. Anthony Don Michael, 4109 Sill Pl., Bakersfield, Calif. 93306

[21] Appl. No.: 105,632

[22] Filed: Aug. 13, 1993

[51] Int. Cl.$^6$ ............................................. A61M 29/00
[52] U.S. Cl. .................................... 601/101; 606/194
[58] Field of Search ............................. 604/101, 102; 606/191–194

[56] References Cited

U.S. PATENT DOCUMENTS

| | | | |
|---|---|---|---|
| 4,636,195 | 1/1987 | Wollinsky | 604/101 |
| 4,932,956 | 6/1990 | Reddy et al. | 606/192 |
| 5,090,960 | 2/1992 | Michael | 604/101 |
| 5,195,955 | 3/1993 | Michael | 604/101 |
| 5,213,577 | 5/1993 | Kratzer | 606/194 |

*Primary Examiner*—Jerome L. Kruter
*Attorney, Agent, or Firm*—Spensley Horn Jubas & Lubitz

[57] ABSTRACT

In a device for dissolving deposits on a wall of a body passage, which wall has openings leading to side passages which device comprises: a catheter having an axis, an outer surface, a distal end and a proximal end, the catheter being insertable into the body passage via the distal end; the catheter having a dissolution agent delivery passage for delivering a dissolution agent to a region surrounding the catheter, and the catheter further having means defining at least one balloon inflation passage; and a balloon secured to the outer surface of the catheter at a location spaced from the dissolution agent delivery passage and communicating with the at least one balloon inflation passage, the balloon being inflatable to at least partly block a space between the catheter and the body passage wall when the catheter is inserted into the body passage, the improvement wherein the balloon has a nonuniform compliance such that when an inflation fluid is supplied to the balloon, the balloon expands parallel to the axis to a greater degree into the region than away from the region.

16 Claims, 2 Drawing Sheets

OBSTRUCTION DISSOLUTION CATHETER WITH VARIABLY EXPANDING BLOCKING BALLOONS AND METHOD OF USE

BACKGROUND OF THE INVENTION

The present invention relates to the treatment of deposits forming obstructions in body passages, such as blood vessels, and particularly to the removal of such deposits by chemical dissolution. The invention also relates to other types of treatment of limited regions of a body passage wall.

It has previously been proposed to effect various treatments on isolated portions of the walls of body passages including, but not limited to, blood vessels. For example, certain materials, such as plaque, form deposits on blood vessel walls. These deposits can become sufficiently large to significantly impede the flow of blood, thereby creating a life threatening medical condition. In addition, when performing treatments associated with the removal of plaque, or the treatment of other conditions in blood vessels, it may be desired to bring a treatment material into contact with an isolated portion of a body passage wall for an extended period of time.

It frequently occurs that the location where treatment is to be performed is in close proximity to a side branch of the body passage. Unless such a side branch is blocked, the treatment agent brought into contact with the body passage wall will flow off via that side branch.

It has been proposed, as disclosed in U.S. Pat. No. 5,176,638, to isolate a body passage region by means of a catheter provided with two blocking balloons, or other blocking devices, which isolate a region to be treated from the remainder of the body passage. If the balloons of such a catheter system happen to be properly positioned relative to any adjacent side branches, the balloons can also act to block those branches.

However, with the devices previously disclosed, use is made of balloons which, upon expansion, are inflated essentially radially, and possibly circumferentially. Therefore, these balloons can act on a side branch which is not outside the treatment region only if the balloon is directly aligned with the side branch. If, on the other hand, the side branch is offset somewhat from the balloon and is located essentially within the treatment region, it cannot be blocked.

SUMMARY OF THE INVENTION

It is an object of the present invention to construct devices of the type described above to improve their ability to block any side branches which may be in proximity to the portion of a wall of a body passage which is to be treated.

Another object of the invention is to provide a device which can be easily controlled to block side branches even if they are in immediate proximity to the region to be treated.

The above and other objects are achieved, according to the present invention, in a device for dissolving deposits on a wall of a body passage, which wall has openings leading to side passages which device comprises:

a catheter having an axis, an outer surface, a distal end and a proximal end, the catheter being insertable into the body passage via the distal end;

the catheter having a dissolution agent delivery passage for delivering a dissolution agent to a region surrounding the catheter, and the catheter further having means defining at least one balloon inflation passage; and a balloon secured to the outer surface of the catheter at a location spaced from the dissolution agent delivery passage and communicating with the at least one balloon inflation passage, the balloon being inflatable to at least partly block a space between the catheter and the body passage wall when the catheter is inserted into the body passage, by the improvement wherein the balloon has a nonuniform compliance such that when an inflation fluid is supplied to the balloon, the balloon expands parallel to the axis to a greater degree into the region than away from the region.

In further accordance with the invention, the device described above further comprises a second balloon secured to the outer surface of the catheter at a location spaced from the dissolution agent delivery passage so that the dissolution agent delivery passage is positioned between the balloons, the second balloon communicating with the at least one balloon inflation passage and being inflatable to at least partly block a space between the catheter and the body passage wall when the catheter is inserted into the body passage, wherein the second balloon has a nonuniform compliance such that when an inflation fluid is supplied to the second balloon, the second balloon expands parallel to the axis to a greater degree into the region than away from the region.

The objects according to the invention are further achieved by a method for dissolving a deposit on a wall of a body passage, which wall has an opening leading to a side passage, the opening being in proximity to the deposit, using one of the devices described above, comprising:

inserting the catheter into the body passage so that the dissolution agent delivery passage is in proximity to the deposit and the opening is between the balloon and the deposit;

inflating the balloon to an extent sufficient to cause the balloon to obturate the opening; and delivering a dissolution agent to the deposit.

DESCRIPTION OF THE PREFERRED EMBODIMENTS

Figure 1:
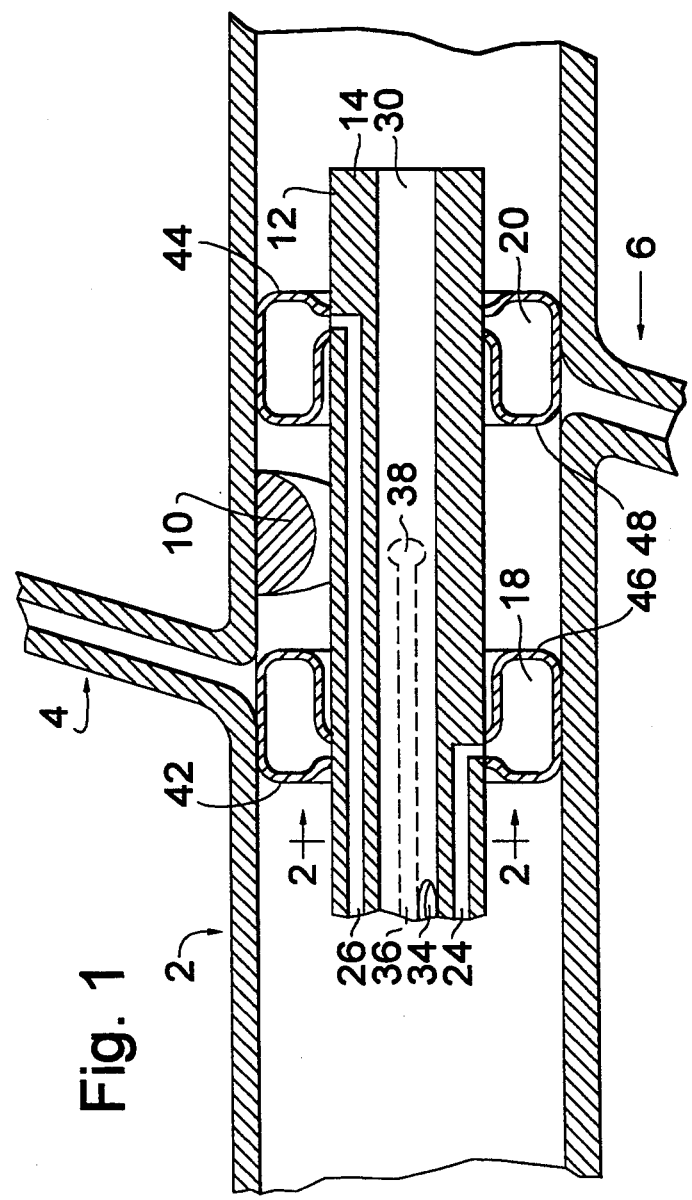
FIG. 1 is a side cross-sectional view illustrating one embodiment of a device according to the invention positioned in a blood vessel.

FIG. 1 illustrates a blood vessel 2, such as a coronary artery, from which there extend two side branches 4 and 6. On the inner wall of blood vessel 2, there has accumulated a deposit 10 composed of plaque. Without medical intervention, it is likely that this deposit will continue to grow until it eventually presents a substantial obstruction to blood flow through vessel 2.

In the example illustrated in FIG. 1, there is a very short distance, along the axis of vessel 2, between deposit 10 and each of branches 4 and 6. In addition, there is only a short axial distance between branches 4 and 6 themselves. Because of this short distance, it would be difficult, with previously proposed catheters, to isolate the region of deposit 10 from the rest of vessel 2 and from side branches 4 and 6.

The embodiment of the invention illustrated in FIG. 1 includes a catheter 12 having a distal end 14 via which catheter 12 is inserted into vessel 2. Catheter 12 further has a proximal end (not shown) which will be located outside of the patient's body when catheter 12 is being employed for a medical procedure.

Catheter 12 carries two blocking balloons 18 and 20 which are mounted on the outer wall of catheter 12 at locations which are spaced apart along the axis of catheter 12. The interior of balloon 18 communicates with a first balloon inflation passage 24, while the interior of balloon 20 communicates with a second balloon inflation passage 26. Each of passages 24 and 26 includes a lumen which extends to the proximal end of catheter 14 where inflation fluid may be supplied at a controlled rate and pressure.

Catheter 12 further includes a central lumen 30 which opens at distal end 14 to provide a blood bypass flow passage between an opening 34 which extends to the outer wall of catheter 12 and distal end 14. Since opening 34 is located out of the region which will be enclosed by balloons 18 and 20, it assures the flow of blood through central lumen 30 from a location to one side of the region enclosed by balloons 18 and 20 to a location at the other side thereof.

Finally, catheter 14 includes a dissolution agent delivery passage 36 which extends to an opening 38 in the outer wall of catheter 12 at a location between balloons 18 and 20. Opening 38 may be surrounded with a flow controlling member such as a member 8 or 40 disclosed in U.S. Pat. No. 5,176,638, cited above.

In order to dissolve deposit 10, catheter 12 is inserted, starting with distal end 14, into vessel 2 until balloons 18 and 20 straddle the location of deposit 10. Balloons 18 and 20 are then inflated in order to isolate the region of vessel 2 where deposit 10 is located from the remainder of the interior of vessel 2.

As disclosed in U.S. Pat. No. 5,163,905, balloons 18 and 20 are of the type known as high compliance volume balloons. Balloons of this type stretch easily during inflation so that they will tend to expand to fill the available volume rather than applying any significant radial pressure to a surface with which they come in contact. This behavior of high compliance volume balloons is described in U.S. Pat. No. 5,195,955.

When the region surrounding a deposit 10 is isolated from the remainder of the interior of blood vessel 2, the presence of side branches at locations which are outside of the isolated region are of no concern because any significant flow of dissolution agent to those side branches is prevented by inflated balloons 18 and 20. If, however, as shown in FIG. 1, side branches 4 and 6 are relatively close to the region to be isolated, it becomes more difficult, and sometimes impossible in the prior art, to position catheter 14 in such a manner as to assure that the side branches will be adequately closed off. If one worked to attempt to achieve this by placing balloons 18 and 20 very close together, the result would be that the catheter would only be capable of establishing an isolated region having a very small axial dimension, which may not enclose the entire deposit 10 and/or would increase the difficulty of establishing the desired chemical balance in the isolated region.

According to the present invention, balloons 18 and 20 are each constructed to have a preferential direction of axial expansion toward the interior of the region between balloons, which region is to be isolated from the remainder of the passage. Specifically, as shown in FIG. 1, where each of balloons 18 and 20 is inflated to an extent to substantially prevent fluid flow past the balloons, each balloon has been fabricated so that during inflation it tends to expand axially toward the other balloon to a greater extent than away from the other balloon. In the embodiment illustrated in FIG. 1, this is achieved by giving each balloon 18 and 20 a greater wall thickness in the balloon portion 42, 44 which faces away from the other balloon than in the balloon portion 46, 48 which faces toward the other balloon. Thus, upon inflation, each balloon 18, 20 will tend to expand radially in order to contact the wall of passage 2 and will also tend to expand axially toward the other balloon. Each balloon 18, 20 can be caused to expand axially to an extent to sufficiently block a side branch such as 4 or 6 which is close to deposit 10.

In practice, the existence of a side branch can be determined by introducing a suitable radiopaque dye via lumen 36 and opening 38 after balloons 18 and 20 have been inflated to an extent sufficient to isolate the intended treatment region. Observation of flow of the radiopaque dye with fluoroscopic apparatus allows flow into a side branch to be observed. While this is being observed, the appropriate balloon 18, 20 may be further inflated until the cessation of such flow has been observed. The intended dissolution treatment can then be performed.

It is a common practice to fabricate balloons by injecting elastic material into a mold. In order to form balloons of the type contemplated by the present invention, it would only be necessary to configure the mold to produce the desired wall thicknesses.

According to another embodiment of the invention, balloons 18 and 20 could have a constant wall thickness, but with portions 42, 44 having a composition different from portions 46, 48. For example, portions 46 and 48 could be made from a material which has been formulated to have a higher level of inherent elasticity, or a higher compliance, than portions 42 and 44. In order to fabricate balloons according to this embodiment, it would simply be necessary to provide the balloon mold with two diametrically opposed material inlets and to introduce different material formulations via the different inlets so that the material introduced via one inlet forms portion 42, 44, while the material introduced via the other inlet forms portion 46, 48. Sufficient material would be introduced to assure that the materials introduced via the two inlets merge at an interface region between portions 42, 44, on the one hand and 46, 48, on the other hand.

Figure 2:
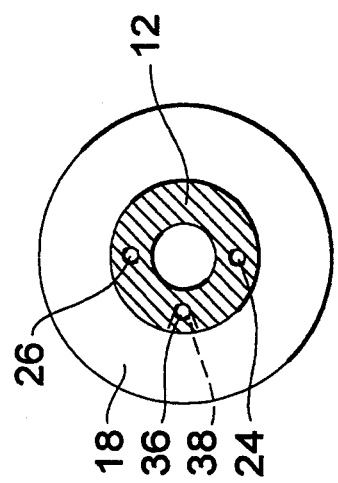
FIG. 2 is a cross-sectional view, taken along the line 2—2 of FIG. 1.

While in the embodiment shown in FIGS. 1 and 2, each balloon 18, 20 is in the form of an annular cuff, each balloon could also be an eccentrically mounted balloon which, upon being inflated, expands circumferentially as well as radially and axially. Such eccentric balloons are disclosed, for example, in U.S. Pat. No. 5,163,905.

Figure 3A:
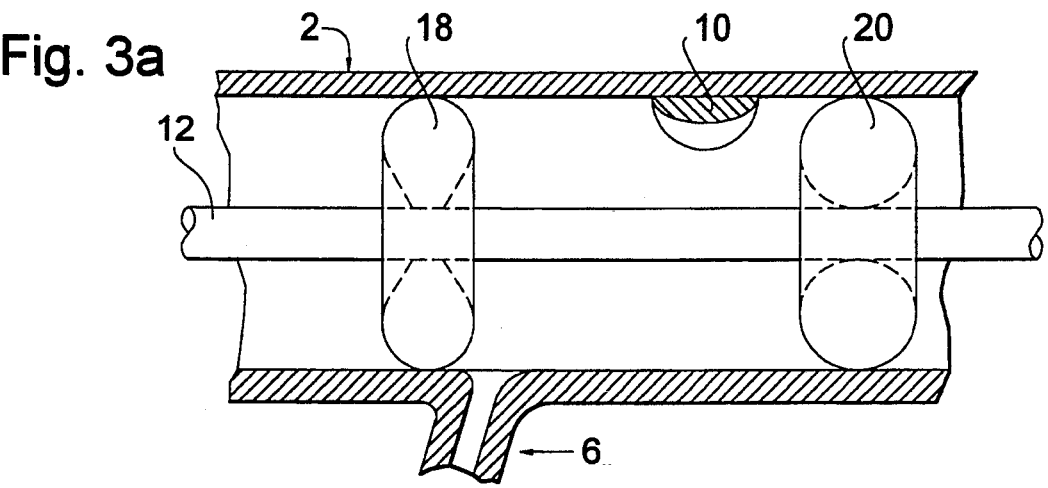
FIGS. 3a–3c are partially cross-sectional views illustrating successive operating states of the embodiment of FIGS. 1 and 2.
Figure 3B:
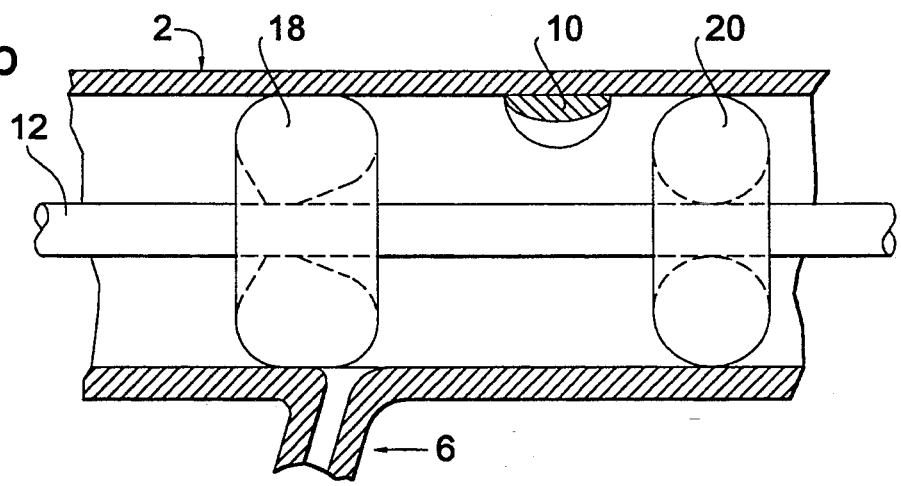
Figure 3C:
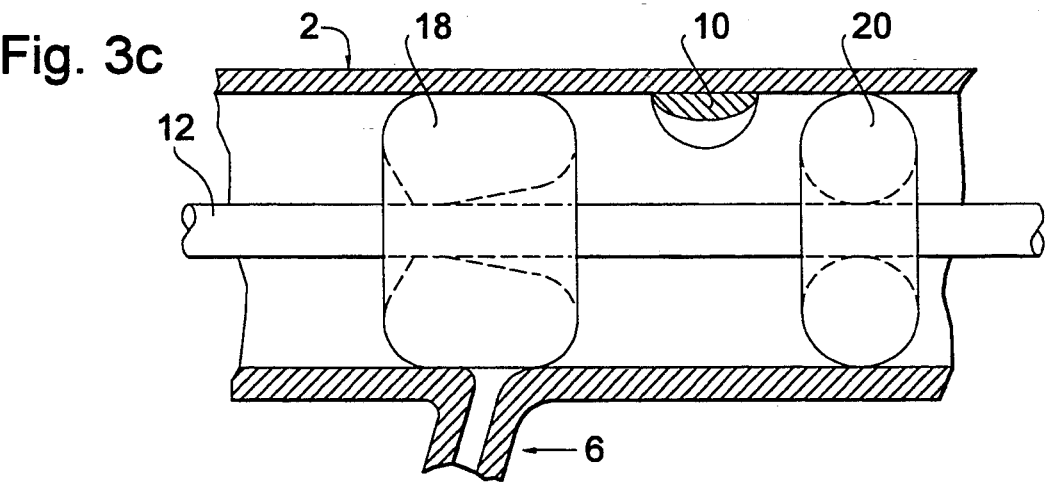

FIGS. 3a–3c illustrate three successive expansion states of balloon 18 of the embodiment of FIGS. 1 and 2. Vessel 2 and side branch 6 are shown in cross section, while catheter 12 and balloons 18 and 20 are shown in elevation. However, the parts of catheter 12 and a portion of the outline of balloons 18 and 20 which are hidden by the inflated balloons are shown in broken lines. Balloon 20 is shown to be inflated sufficiently to block vessel 2.

In FIG. 3a, balloon 18 has been inflated to the minimum amount needed to block vessel 2. Balloon 18 does not intersect the cross section of side branch 6 so that side branch 6 is in full communication with the region where deposit 10 is located.

In FIG. 3b, balloon 18 has been inflated by an additional amount so that it partially obstructs side branch 6. In this state, flow of fluid from the region where deposit 10 is located into side branch 6 will be reduced but not completely impeded.

In FIG. 3c, balloon 18 has been inflated still further so that it substantially completely obstructs side branch 6. In this state of balloon 18, flow of fluid from the region where deposit 10 is located into side branch 6 is substantially completely blocked.

One advantage of devices according to the present invention resides in the ability to inflate each balloon individually. This means that if one balloon must be inflated to a greater degree to block a side branch, the other balloon can be inflated axially to a minimal extent in order to assure that the isolated region retains a volume sufficient to allow accurate control of the chemical composition in that region.

As concerns the dissolution procedure which can be employed with the apparatus according to the present invention, this could be carried out in the manner described in U.S. Pat. Nos. 5,163,905 and 5,176,638.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. In a device for dissolving deposits on a wall of a body passage, which wall has openings leading to side passages, which device comprises:
   a catheter having an axis, an outer surface, a distal end and a proximal end, the catheter being insertable into the body passage via the distal end;
   the catheter having a dissolution agent delivery passage for delivering a dissolution agent to a region surrounding the catheter, and the catheter further having means defining at least one balloon inflation passage; and
   a balloon secured to the outer surface of the catheter at a location spaced from the dissolution agent delivery passage and communicating with the at least one balloon inflation passage, the balloon being inflatable to at least partly block a space between the catheter and the body passage wall when the catheter is inserted into the body passage, the improvement wherein said balloon has a nonuniform compliance such that when an inflation fluid is supplied to said balloon, said balloon expands parallel to said axis to a greater degree into said region than away from said region.

2. A device as defined in claim 1 wherein said balloon has a first wall portion which faces toward said region and a second wall portion which faces away from said region, and said first wall portion has a higher compliance than said second wall portion.

3. A device as defined in claim 2 wherein said first wall portion is thinner than said second wall portion.

4. A device as defined in claim 2 wherein said first wall portion is of a composition having a greater elasticity than said second wall portion.

5. A device as defined in claim 2 wherein said balloon is a high compliance volume balloon.

6. A device as defined in claim 1 further comprising a second balloon secured to the outer surface of the catheter at a location spaced from the dissolution agent delivery passage so that the dissolution agent delivery passage is positioned between said balloons, said second balloon communicating with the at least one balloon inflation passage and being inflatable to at least partly block a space between the catheter and the body passage wall when the catheter is inserted into the body passage, wherein said second balloon has a nonuniform compliance such that when an inflation fluid is supplied to said second balloon, said second balloon expands parallel to said axis to a greater degree into said region than away from said region.

7. A device as defined in claim 6 wherein said second balloon has a first wall portion which faces toward said region and a second wall portion which faces away from said region, and said first wall portion has a higher compliance than said second wall portion.

8. A device as defined in claim 7 wherein said first wall portion is thinner than said second wall portion.

9. A device as defined in claim 7 wherein said first wall portion is of a composition having a greater elasticity than said second wall portion.

10. A device as defined in claim 7 wherein said balloon is a high compliance volume balloon.

11. A method for dissolving a deposit on a wall of a body passage, which wall has an opening leading to a side passage, the opening being in proximity to the deposit, using the device defined in claim 1, comprising:
   inserting the catheter into the body passage so that the dissolution agent delivery passage is in proximity to the deposit and the opening is between the balloon and the deposit;
   inflating the non-uniform compliant balloon to an extent sufficient to cause the balloon to obturate the opening; and
   delivering a dissolution agent to the deposit 12. A method as defined in claim 11 wherein said step of inflating comprises monitoring the location of the opening relative to the balloon to confirm obturation of the opening.

13. A method as defined in claim 11 wherein said step of inflating is performed to cause the balloon to completely block the opening.

14. A device as defined in claim 1 further comprising a second balloon secured to the outer surface of the catheter at a location spaced from the dissolution agent delivery means so that the dissolution agent delivery passage is positioned between said balloons and said region extends between said balloons.

15. A device as defined in claim 1 wherein the nonuniform compliance of said balloon is such that when an inflation fluid is supplied to said balloon, said balloon expands parallel to said axis to a greater degree toward said dissolution agent delivery passage than away from said dissolution agent delivery passage.

16. A method as defined in claim 11 wherein said step of inflating the non-uniform compliant balloon comprises causing the balloon to expand parallel to the axis of the catheter to a greater degree toward the dissolution agent delivery passage than away from the dissolution agent delivery passage.

* * * * *